US 10,935,174 B2

United States Patent
Pennybacker et al.

(10) Patent No.: US 10,935,174 B2
(45) Date of Patent: Mar. 2, 2021

(54) STRESS RELIEF COUPLINGS FOR CRYOTHERAPY APPARATUSES

(71) Applicant: Zeltiq Aesthetics, Inc., Pleasanton, CA (US)

(72) Inventors: William P. Pennybacker, Livermore, CA (US); Craig Carson, Fremont, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 922 days.

(21) Appl. No.: 14/829,424

(22) Filed: Aug. 18, 2015

(65) Prior Publication Data
US 2016/0051308 A1    Feb. 25, 2016

Related U.S. Application Data

(60) Provisional application No. 62/039,194, filed on Aug. 19, 2014.

(51) Int. Cl.
*A61B 18/14* (2006.01)
*F16L 27/02* (2006.01)
(Continued)

(52) U.S. Cl.
CPC .............. *F16L 27/02* (2013.01); *A61M 39/10* (2013.01); *A61B 2018/00172* (2013.01); *A61M 2039/1033* (2013.01)

(58) Field of Classification Search
CPC ..... F16L 27/02; F16L 33/225; F16L 27/0812; A61M 39/10; A61M 2039/1033; A61B 2018/00178; A61B 2018/00172
See application file for complete search history.

(56) References Cited

U.S. PATENT DOCUMENTS

| 681,806 A | 9/1901 | Mignault et al. |
| 889,810 A | 6/1908 | Robinson et al. |

(Continued)

FOREIGN PATENT DOCUMENTS

| AU | 2011253768 A1 | 6/2012 |
| CA | 2441489 A1 | 3/2005 |

(Continued)

OTHER PUBLICATIONS

"ThermaCool Monopolar Capacitive Radiofrequency, the one choice for nonablative tissue tightening and contouring", Thermage, Inc. Tech Brochure, Nov. 30, 2005, 8 pgs.

(Continued)

*Primary Examiner* — Jaymi E Della
(74) *Attorney, Agent, or Firm* — Perkins Coie LLP

(57) ABSTRACT

Systems, devices, and methods for treating a patient are disclosed. The systems can include a cryotherapy apparatus for selectively treating targeted tissue. The cryotherapy apparatus includes one or more stress relief couplings located along a conduit to help keep an applicator positioned at a treatment site without significant rotational torque being imparted to the applicator by the conduit so that the applicator does not tend to move relative to patient skin during a tissue treatment. The stress relief couplings can include swivel connectors and clamps that cooperate to minimize or limit a rotational force exerted on the applicator by the conduit after the applicator is applied to the patient's skin.

20 Claims, 5 Drawing Sheets

(51) Int. Cl.
*A61M 39/10* (2006.01)
*A61B 18/00* (2006.01)

(56) References Cited

U.S. PATENT DOCUMENTS

| | | | |
|---|---|---|---|
| 1,093,868 | A * | 4/1914 | Leighty ............... F16L 19/04 |
| | | | 123/193.3 |
| 2,516,491 | A | 7/1950 | Swastek |
| 2,521,780 | A | 9/1950 | Dodd et al. |
| 2,726,658 | A | 12/1955 | Chessey |
| 2,766,619 | A | 10/1956 | Tribus et al. |
| 2,851,602 | A | 9/1958 | Cramwinckel et al. |
| 3,093,135 | A | 6/1963 | Hirschhorn |
| 3,132,688 | A | 5/1964 | Nowak |
| 3,133,539 | A | 5/1964 | Eidus et al. |
| 3,282,267 | A | 11/1966 | Eidus |
| 3,341,230 | A * | 9/1967 | Wichers ............... F21V 21/30 |
| | | | 285/266 |
| 3,502,080 | A | 3/1970 | Hirschhorn |
| 3,587,577 | A | 6/1971 | Zubkov et al. |
| 3,591,645 | A | 7/1971 | Selwitz |
| 3,692,338 | A * | 9/1972 | Nick ............... F16L 15/04 |
| | | | 285/272 |
| 3,703,897 | A | 11/1972 | Mack et al. |
| 3,710,784 | A | 1/1973 | Taylor |
| 3,786,814 | A | 1/1974 | Armao |
| 3,827,436 | A | 8/1974 | Andera et al. |
| 3,942,519 | A | 3/1976 | Shock |
| 3,948,269 | A | 4/1976 | Zimmer |
| 3,986,385 | A | 10/1976 | Johnston et al. |
| 3,993,053 | A | 11/1976 | Grossan |
| 4,002,221 | A | 1/1977 | Buchalter |
| 4,008,910 | A * | 2/1977 | Roche ............... H02G 3/06 |
| | | | 285/153.1 |
| 4,026,299 | A | 5/1977 | Sauder |
| 4,140,130 | A | 2/1979 | Storm |
| 4,149,529 | A | 4/1979 | Copeland et al. |
| 4,178,429 | A | 12/1979 | Scheffer |
| 4,202,336 | A | 5/1980 | Van Gerven |
| 4,266,043 | A | 5/1981 | Fujii et al. |
| 4,269,068 | A | 5/1981 | Molina |
| 4,381,009 | A | 4/1983 | Del Bon |
| 4,396,011 | A | 8/1983 | Mack et al. |
| 4,459,854 | A | 7/1984 | Richardson et al. |
| 4,470,263 | A | 9/1984 | Lehovec et al. |
| 4,483,341 | A | 11/1984 | Witteles |
| 4,528,979 | A | 7/1985 | Marchenko et al. |
| 4,531,524 | A | 7/1985 | Mioduski |
| 4,548,212 | A | 10/1985 | Leung |
| 4,555,313 | A | 11/1985 | Duchane et al. |
| 4,585,002 | A | 4/1986 | Kissin |
| 4,603,076 | A | 7/1986 | Bowditch et al. |
| 4,614,191 | A | 9/1986 | Perler et al. |
| 4,644,955 | A | 2/1987 | Mioduski |
| 4,664,110 | A | 5/1987 | Schanzlin |
| 4,700,701 | A | 10/1987 | Montaldi |
| 4,718,429 | A | 1/1988 | Smidt |
| 4,741,338 | A | 5/1988 | Miyamae |
| 4,758,217 | A | 7/1988 | Gueret |
| 4,764,463 | A | 8/1988 | Mason et al. |
| 4,802,475 | A | 2/1989 | Weshahy |
| 4,832,022 | A | 5/1989 | Tjulkov et al. |
| 4,846,176 | A | 7/1989 | Golden |
| 4,850,340 | A | 7/1989 | Onishi |
| 4,869,250 | A | 9/1989 | Bitterly |
| 4,880,564 | A | 11/1989 | Abel et al. |
| 4,905,697 | A | 3/1990 | Heggs et al. |
| 4,906,463 | A | 3/1990 | Cleary et al. |
| 4,930,317 | A | 6/1990 | Klein |
| 4,935,345 | A | 6/1990 | Guilbeau et al. |
| 4,961,422 | A | 10/1990 | Marchosky et al. |
| 4,962,761 | A | 10/1990 | Golden |
| 4,990,144 | A | 2/1991 | Blott et al. |
| 5,007,433 | A | 4/1991 | Hermsdoerffer et al. |
| 5,018,521 | A | 5/1991 | Campbell et al. |
| 5,024,650 | A | 6/1991 | Hagiwara et al. |
| 5,065,752 | A | 11/1991 | Sessions et al. |
| 5,069,208 | A | 12/1991 | Noppel et al. |
| 5,084,671 | A | 1/1992 | Miyata et al. |
| 5,108,390 | A | 4/1992 | Potocky et al. |
| 5,119,674 | A | 6/1992 | Nielsen |
| 5,139,496 | A | 8/1992 | Hed |
| 5,143,063 | A | 9/1992 | Fellner |
| 5,148,804 | A | 9/1992 | Hill et al. |
| 5,158,070 | A | 10/1992 | Dory |
| 5,169,384 | A | 12/1992 | Bosniak et al. |
| 5,197,466 | A | 3/1993 | Marchosky et al. |
| 5,207,674 | A | 5/1993 | Hamilton |
| 5,221,726 | A | 6/1993 | Dabi et al. |
| 5,264,234 | A | 11/1993 | Windhab et al. |
| 5,277,030 | A | 1/1994 | Miller |
| 5,314,423 | A | 5/1994 | Seney et al. |
| 5,327,886 | A | 7/1994 | Chiu |
| 5,330,745 | A | 7/1994 | Mcdow et al. |
| 5,333,460 | A | 8/1994 | Lewis et al. |
| 5,334,131 | A | 8/1994 | Omandam et al. |
| 5,336,616 | A | 8/1994 | Livesey et al. |
| 5,339,541 | A | 8/1994 | Owens |
| 5,342,617 | A | 8/1994 | Gold et al. |
| 5,351,677 | A | 10/1994 | Kami et al. |
| 5,358,467 | A | 10/1994 | Milstein et al. |
| 5,362,966 | A | 11/1994 | Rosenthal et al. |
| 5,363,347 | A | 11/1994 | Nguyen |
| 5,372,608 | A | 12/1994 | Johnson |
| 5,386,837 | A | 2/1995 | Sterzer |
| 5,411,541 | A | 5/1995 | Bell et al. |
| 5,427,772 | A | 6/1995 | Hagan et al. |
| 5,433,717 | A | 7/1995 | Rubinsky et al. |
| 5,456,703 | A | 10/1995 | Beeuwkes, III et al. |
| 5,472,416 | A | 12/1995 | Blugerman et al. |
| 5,486,207 | A | 1/1996 | Mahawili |
| 5,497,596 | A | 3/1996 | Zatkulak |
| 5,501,655 | A | 3/1996 | Rolt et al. |
| 5,505,726 | A | 4/1996 | Meserol |
| 5,505,730 | A | 4/1996 | Edwards et al. |
| 5,507,790 | A | 4/1996 | Weiss |
| 5,514,105 | A | 5/1996 | Goodman, Jr. et al. |
| 5,514,170 | A | 5/1996 | Mauch |
| 5,516,505 | A | 5/1996 | McDow |
| 5,531,742 | A | 7/1996 | Barken |
| 5,558,376 | A * | 9/1996 | Woehl ............... H01R 35/04 |
| | | | 285/91 |
| 5,562,604 | A | 10/1996 | Yablon et al. |
| 5,571,801 | A | 11/1996 | Segall et al. |
| 5,575,812 | A | 11/1996 | Owens et al. |
| 5,603,221 | A | 2/1997 | Maytal |
| 5,628,769 | A | 5/1997 | Saringer |
| 5,634,890 | A | 6/1997 | Morris |
| 5,634,940 | A | 6/1997 | Panyard |
| 5,647,051 | A | 7/1997 | Neer |
| 5,647,868 | A | 7/1997 | Chinn |
| 5,650,450 | A | 7/1997 | Lovette et al. |
| 5,651,773 | A | 7/1997 | Perry et al. |
| 5,654,279 | A | 8/1997 | Rubinsky et al. |
| 5,654,546 | A | 8/1997 | Lindsay et al. |
| 5,660,836 | A | 8/1997 | Knowlton et al. |
| 5,665,053 | A | 9/1997 | Jacobs |
| 5,672,172 | A | 9/1997 | Zupkas |
| 5,700,284 | A | 12/1997 | Owens et al. |
| 5,725,483 | A | 3/1998 | Podolsky |
| 5,733,280 | A | 3/1998 | Avitall |
| 5,741,248 | A | 4/1998 | Stern et al. |
| 5,746,702 | A | 5/1998 | Gelfgat et al. |
| 5,746,736 | A | 5/1998 | Tankovich |
| 5,755,663 | A | 5/1998 | Larsen et al. |
| 5,755,753 | A | 5/1998 | Knowlton et al. |
| 5,755,755 | A | 5/1998 | Panyard |
| 5,759,182 | A | 6/1998 | Varney et al. |
| 5,759,764 | A | 6/1998 | Polovina et al. |
| 5,769,879 | A | 6/1998 | Richards et al. |
| 5,785,955 | A | 7/1998 | Fischer |
| 5,792,080 | A | 8/1998 | Ookawa et al. |
| 5,800,490 | A | 9/1998 | Patz et al. |
| 5,814,040 | A | 9/1998 | Nelson et al. |

(56) References Cited

U.S. PATENT DOCUMENTS

| | | |
|---|---|---|
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,853,364 A | 12/1998 | Baker, Jr. et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |

(56) References Cited

U.S. PATENT DOCUMENTS

| | | |
|---|---|---|
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |

(56) References Cited

U.S. PATENT DOCUMENTS

| | | |
|---|---|---|
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1* | 5/2006 | Boutillette ......... A61B 1/00128 600/136 |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |

(56) References Cited

U.S. PATENT DOCUMENTS

| | | |
|---|---|---|
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Edoute et al. |
| 2013/0245507 A1 | 9/2013 | Khorassani |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |

(56) References Cited

FOREIGN PATENT DOCUMENTS

| | | |
|---|---|---|
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

(56) References Cited

OTHER PUBLICATIONS

Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002,pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.

Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: the Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.

(56) References Cited

OTHER PUBLICATIONS

Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/material-science-;products.htmi?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

* cited by examiner

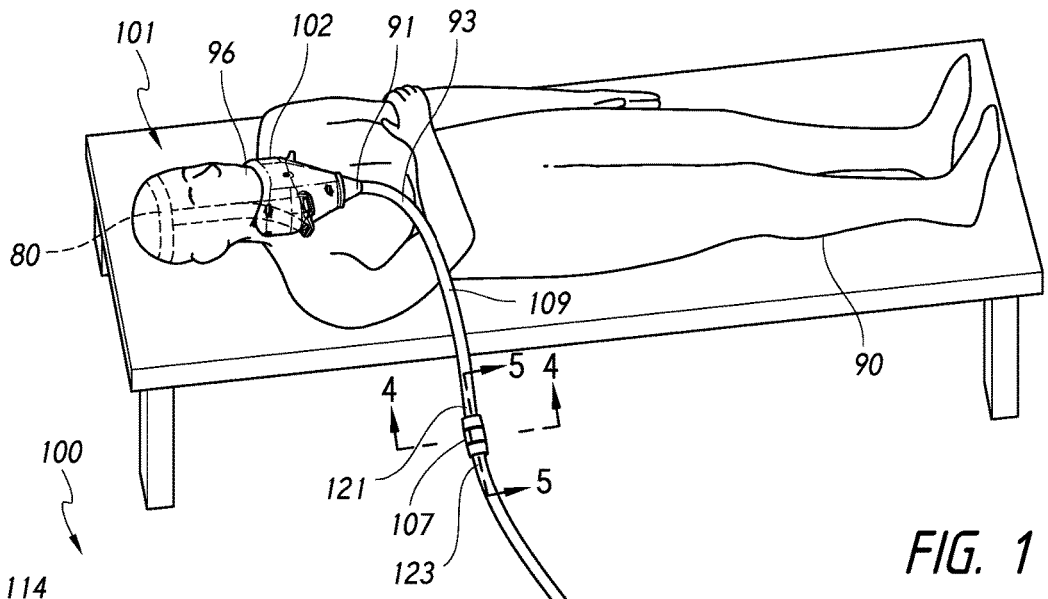
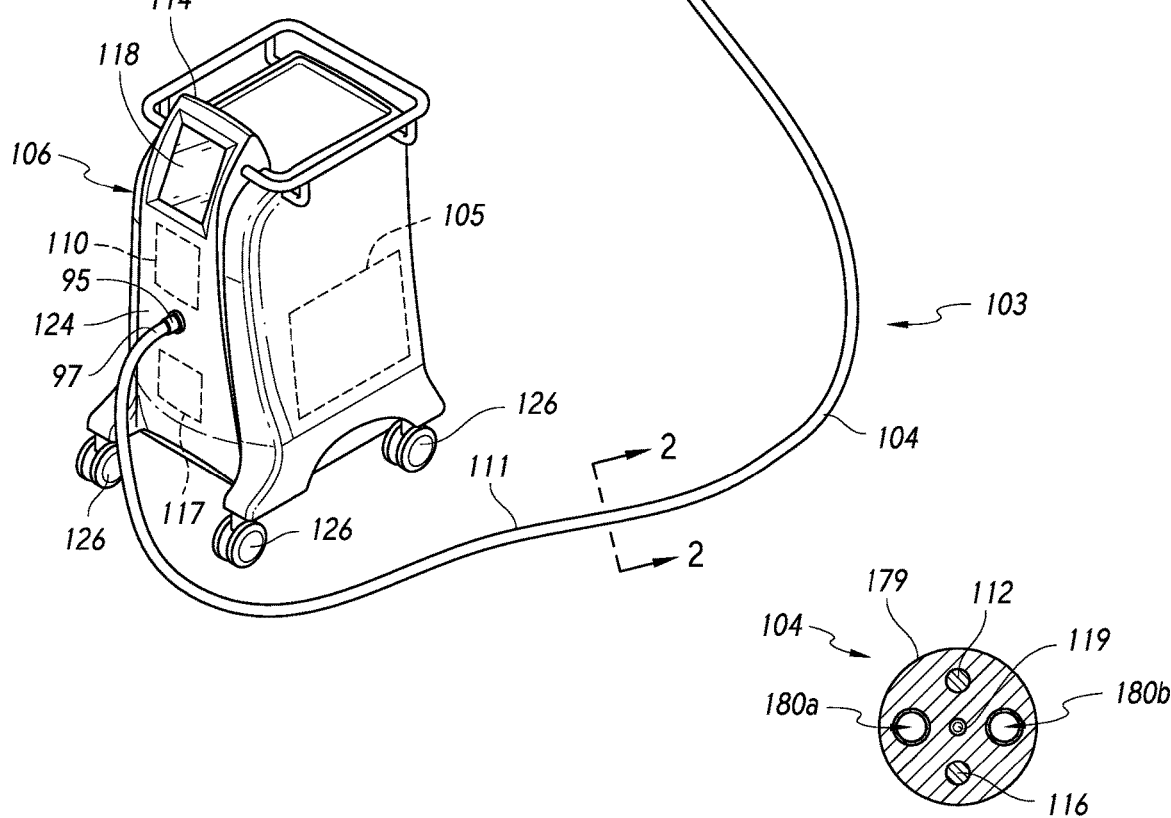
FIG. 1
FIG. 2

STRESS RELIEF COUPLINGS FOR CRYOTHERAPY APPARATUSES

CROSS-REFERENCE TO RELATED APPLICATION

The present application claims the benefit of U.S. Provisional Patent Application No. 62/039,194, filed Aug. 19, 2014, which is incorporated herein by reference in its entirety.

INCORPORATION BY REFERENCE OF COMMONLY-OWNED APPLICATIONS AND PATENTS

The following commonly assigned U.S. patent applications and U.S. patents are incorporated herein by reference in their entireties:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Patent Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Patent Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Patent Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. Patent Publication No. 2014/0277219 entitled "MULTI-MODALITY TREATMENT SYSTEMS, METHODS AND APPARATUS FOR ALTERING SUBCUTANEOUS LIPID-RICH TISSUE";

U.S. Patent Publication No. 2014/0277302 entitled "TREATMENT SYSTEMS WITH FLUID MIXING SYSTEMS AND FLUID-COOLED APPLICATORS AND METHODS OF USING THE SAME";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE;" and U.S. Pat. No. 8,285,390 entitled "MONITORING THE COOLING OF SUBCUTANEOUS LIPID-RICH CELLS, SUCH AS THE COOLING OF ADIPOSE TISSUE."

TECHNICAL FIELD

The present disclosure relates generally to treatment systems for treating patients. Several embodiments are directed to stress relief couplings for cryotherapy apparatuses capable of reducing or eliminating tissue.

BACKGROUND

Excess body fat, or adipose tissue, may be present in various locations of the body, including, for example, the thigh, buttocks, abdomen, knees, back, face, arms, and other areas. Excess adipose tissue can detract from personal appearance and athletic performance. Excess subcutaneous fat under the chin and/or around the neck can be cosmetically unappealing and, in some instances, can produce a "double chin" that may cause stretching and/or sagging of skin. Excess adipose tissue in superficial fat compartments can also produce loose facial structures, such as loose jowls. Excess adipose tissue is thought to magnify the unattractive appearance of cellulite, which forms when subcutaneous fat lobules protrude or penetrate into the dermis and create dimples where the skin is attached to underlying structural fibrous strands. Cellulite and excessive amounts of adipose tissue are often considered to be cosmetically unappealing. Moreover, significant health risks may be associated with higher amounts of excess body fat.

Aesthetic improvement of the human body often involves the selective removal of adipose tissue. Removal of excess adipose tissue has been reported to have health benefits in addition to the cosmetic enhancements. Currently, the most common procedures for this purpose are invasive, such as liposuction or other surgical techniques. Invasive procedures, however, tend to be associated with high cost, long recovery times, and increased risk of complications. In many instances, non-invasive or minimally invasive procedures can allow some or all of these disadvantages to be avoided while providing at least comparable clinical outcomes as those of invasive procedures. For example, non-invasive removal of excess subcutaneous adipose tissue can eliminate both unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. Additional methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING."

BRIEF DESCRIPTION OF THE DRAWINGS

In the drawings, identical reference numbers identify similar elements or acts.

FIG. 1 is a partially schematic, isometric view of a treatment system for affecting target regions of a subject in accordance with an embodiment of the technology.

FIG. 2 is a cross-sectional view of a connector taken along line 2-2 of FIG. 1.

DETAILED DESCRIPTION

A. Overview

Figure 3:
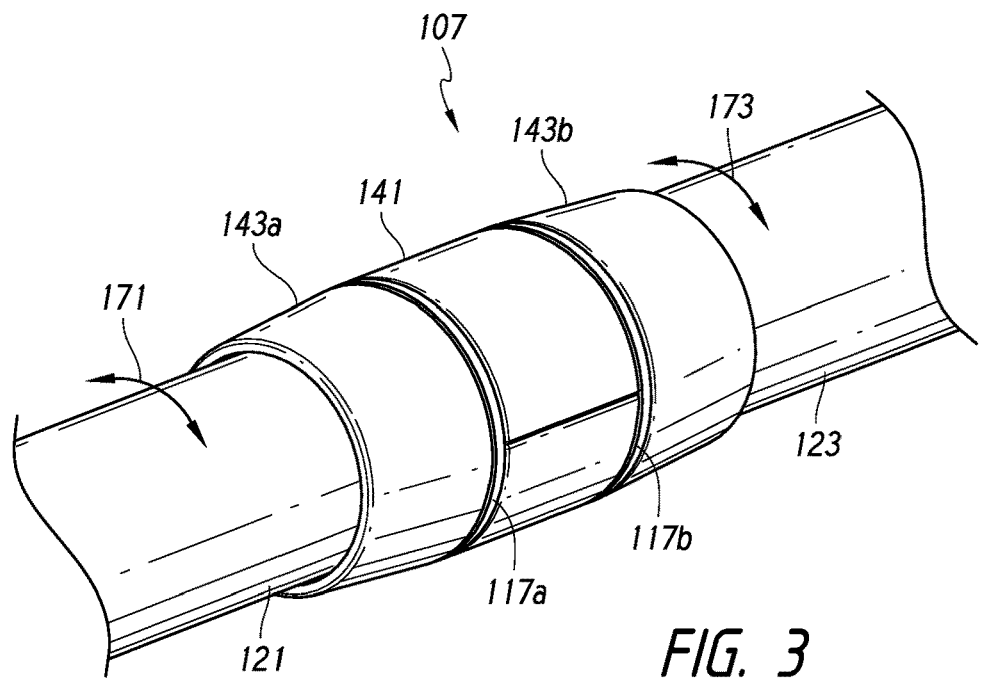
FIG. 3 is an isometric view of a stress relief coupling connected to a conduit in accordance with some embodiments of the technology.

The present disclosure describes treatment systems and couplings for connecting components. Several embodiments are directed to stress relief couplings configured to relieve stresses to minimize or limit forces being applied to applicators that would cause movement of the applicators relative to target sites. The stress relief couplings can be located along conduits connecting components of treatment apparatuses. Several of the details set forth below are provided to describe the following examples and methods in a manner sufficient to enable a person skilled in the relevant art to practice, make, and use them. Several of the details and advantages described below, however, may not be necessary to practice certain examples and methods of the technology. Additionally, the technology may include other examples and uses that are within the scope of the technology but are not described in detail.

At least some embodiments of the present technology are an apparatus for selectively treating targeted tissue. The apparatus can include one or more couplings located along a conduit to help keep an applicator positioned at a treatment site in a fixed non-movable location. The couplings can include swivel connectors and clamps that cooperate to minimize or limit a rotational force exerted on the applicator by the conduit after the applicator is applied to the patient's skin. The couplings can preferably be used with submental applicators. If a submental applicator moves relative to the patient skin during a treatment, the target tissue may be under treated and/or non-targeted tissue (e.g., tissue next to targeted submental tissue) may be treated. This is because a relative small volume of target tissue is drawn into submental applicators.

In some embodiments, an apparatus for selectively treating target tissue includes one or more stress relief couplings located along a conduit to help keep a patient device (e.g., an applicator) positioned at a treatment site. The stress relief couplings can include swivel connectors and clamps that cooperate to minimize or limit rotational forces exerted on the patient device by the conduit after the patient device is applied to the patient. The conduit can be rigid or flexible and can contain one or more lines, electrical wires, hoses, tubes, and/or other components for interconnecting the patient device and a base unit.

In certain embodiments, a stress relief coupling is configured to be attached to a conduit that interconnects an applicator and the base unit such that the base unit, applicator, and conduit are usable to treat a patient when the applicator is applied to the patient's skin. The stress relief coupling can include swivel connectors and a clamp that together can have one or more features for limiting relative motion. The features can include tabs, stops, or other structural features that allow the swivel connectors to rotate relative to each other through a predetermined angle (e.g., about 20 degrees to about 340 degrees). In some embodiments, the angle is between about 45 degrees to about 315 degrees, about 90 degrees to about 270 degrees, about 135 degrees to about 225 degrees, or about 160 degrees to about 200 degrees. Additionally, the stress relief coupling can be attached to the conduit at a location spaced apart from a location where the conduit connects to the applicator so that significant rotational forces are not exerted on connections between elements housed in the conduit and the applicator when the swivel connectors rotate relative to one another.

In further embodiments, an apparatus for treating a patient comprises an applicator, a conduit, and a stress relief coupling. The conduit contains one or more elements (e.g., electrical wires and tubing) connected to the applicator and another component (e.g., a base unit). In some embodiments, the stress relief coupling is directly or indirectly connected to the conduit at a location displaced and remote from the applicator and a base unit to allow a conduit section located between the applicator and the stress relief coupling to rotate relative to another conduit section located between the stress relief coupling and the base unit. According to some embodiments the stress relief coupling has swivel connectors connected to ends of the conduit by, for example, adhesive, fasteners (e.g., screws, pins, etc.), retaining clamps, combinations thereof, or other suitable components for inhibiting relative movement. In some embodiments, retaining clamps hold the conduit ends against external threads of the swivel connectors.

The term "treatment system", as used generally herein, refers to cosmetic or medical treatment systems, as well as any treatment regimens or medical device usage. Some of the embodiments disclosed herein can be for cosmetically beneficial alterations of target regions. For example, stress relief couplings disclosed herein can be part of an apparatus for performing cosmetic procedures. Some cosmetic procedures may be for the sole purpose of altering the body region to conform to a cosmetically desirable look, feel, size, shape and/or other desirable cosmetic characteristic or feature. Accordingly, at least some embodiments of the cosmetic procedures can be performed without providing an appreciable therapeutic effect (e.g., no therapeutic effect).

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. The headings provided herein are for convenience only and are not intended to limit or interpret the scope or meaning of the technology.

B. Treatment Systems and Cryotherapy

FIG. 1 and the following discussion provide a brief, general description of a treatment system in the form of an apparatus 100 for cooling tissue in accordance with some embodiments of the technology. The apparatus 100 can include a non-invasive applicator 102 ("applicator 102"), a connector 103, and a base unit 106. The applicator 102 can conform closely to the contours of the subject's body 101 to treat a target site. The connector 103 can be an umbilical cord that provides suction for drawing tissue into the applicator 102 and energy (e.g., electrical energy) and fluid (e.g., coolant) from the base unit 106 to the applicator 102. In some embodiments, the applicator 102 can be a relatively small applicator positionable generally under the subject's chin 96 to treat a small region of targeted submental tissue. The submental tissue can be sufficiently cooled to reduce or eliminate the subcutaneous adipose tissue to reduce or eliminate a double chin (or loose jowls) while non-targeted tissue (e.g., non-fat tissue of the neck and/or face) can be generally unaffected.

The connector 103 can include a conduit 104 and a stress relief coupling 107 ("coupling 107") that minimizes, reduces, or substantially eliminates forces (e.g., forces applied by the conduit 104 to the applicator 102) that would cause the applicator 102 to move an undesirable amount before and/or during cryotherapy. Conduit ends 121, 123 can rotate relative to one another to minimize, limit, or substantially eliminate stresses (e.g., stresses caused by twisting) in the conduit 104, particularly at its connection to the applicator 102. As such, the conduit 104 can be moved between a wide range of configurations without imparting appreciable rotational forces to the applicator 102 so as to minimize, limit, or substantially eliminate twisting or other undesired movement of the applicator 102. Accordingly, an operator can move the connector 103 without causing patient discomfort, separation of the applicator 102 from the patient 101, or other problems caused by twisting of the applicator 102.

A fastener 91 can connect a conduit section 109 to the applicator 102 such that an applicator end 93 of the conduit section 109 is rotationally fixed to the applicator 102. The length of the conduit section 109 can be selected to avoid damaging connections between the applicator 102 and internal elements of the conduit section 109. The length of conduit section 109 should not be zero (if the fastener 91 is allowed to rotate the connections between the applicator 102 and the internal elements of the conduit section 109 may fail). On the other hand, if the length of the conduit section 109 is too large (such as the entire length of the conduit 104 if the coupling 107 were placed next to fastener 95), too much rotational torque could be stored in the conduit section 109 causing the applicator 102 to twist during treatment. Hence a preferred length of the section 109 can be less than or greater than 1 ft, 2 ft, 3 ft, 4 ft, or 5 ft. One preferred embodiment is about 2 feet, but other lengths can be used if needed or desired. The fastener 95 can connect a conduit section 111 to the base unit 106 such that a base unit end 97 of the conduit section 111 is rotationally fixed to the base unit 106. Each fastener 91, 95 can include, without limitation, one or more clamps, retainer rings, pins, screws, or combinations thereof. The length of the conduit section 111 can be any length needed to interconnect the applicator 102 and base unit 106.

FIG. 2 is a cross-sectional view of the conduit 104 taken along line 2-2 of FIG. 1 in accordance with at least some embodiments of the technology. The conduit 104 can include a main body 179 (e.g., a solid or hollow main body), a supply fluid line or lumen 180a ("supply fluid line 180a"), and a return fluid line or lumen 180b ("return fluid line 180b"). The main body 179 may be configured (via one or more adjustable joints) to "set" in place for the treatment of the subject. The supply and return fluid lines 180a, 180b can be tubes made of polyethylene, polyvinyl chloride, polyurethane, and/or other materials that can accommodate circulating coolant, such as water, glycol, synthetic heat transfer fluid, oil, a refrigerant, and/or any other suitable heat conducting fluid. In one embodiment, each fluid line 180a, 180b can be a flexible hose surrounded by the main body 179. The conduit 104 can also house one or more electrical lines 112 for providing power to the applicator 102 (FIG. 1) and one or more control lines 116 for providing communication between the base unit 106 (FIG. 1) and the applicator 102 (FIG. 1). To provide suction, the conduit 104 can house one or more vacuum tubes 119.

Referring again to FIG. 1, the base unit 106 can include a fluid chamber or reservoir 105 (illustrated in phantom line) and a controller 114 carried by a housing 125 with wheels 126. The base unit 106 can include a refrigeration unit, a cooling tower, a thermoelectric chiller, heaters, or any other device capable of controlling the temperature of coolant in the fluid chamber 105 and can be connectable to electrical power (e.g., an external power source or an internal power supply 110 shown in phantom line). Coolant can be continuously or intermittently delivered to the applicator 102 via the supply fluid line 180a (FIG. 2) and can circulate through the applicator 102 to absorb heat. The coolant, which has absorbed heat, can flow from the applicator 102 back to the base unit 106 via the return fluid line 180b (FIG. 2). For warming periods, the base unit 106 can heat the coolant such that warm coolant is circulated through the applicator 102. Alternatively, a municipal water supply (e.g., tap water) can be used in place of or in conjunction with the base unit 106. A pressurization device 113 can provide suction to the applicator 102 via the vacuum tube 119 (FIG. 2) and can include one or more pumps. Air pressure can be controlled with a regulator between the pressurization device 113 and the applicator 102. Additionally or alternatively, air pressure may be reduced up to the maximum capacity of the pressurization device 113. If the vacuum level is too low, the tissue will not be drawn adequately (or at all) into the applicator 102 and the applicator 102 may tend to move along the patient's skin. If the vacuum level is too high, undesirable discomfort to the patient and/or tissue damage could occur. According to one embodiment, approximately 0.5 inch Hg, 1 inch Hg, 2 inches Hg, 3 inches Hg, or 5 inches Hg vacuum is applied to draw facial or neck tissue into the applicator 102. Other vacuum levels can be selected based on the characteristics of the tissue and desired level of comfort. A retaining apparatus 80 (shown in dashed line) can help hold the applicator 102 against the subject's skin.

An operator can control operation of the apparatus 100 using an input/output device 118 of the controller 114. The input/output device 118 can display the state of operation of the applicator 102. The power supply 110 can provide a direct current voltage for powering electrical elements (e.g., thermal devices) of the applicator 102 via the electrical line 112 (FIG. 2). In some embodiments, the controller 114 can exchange data with the applicator 102 via a wireless or an optical communication link and can monitor and adjust treatment based on, without limitation, one or more treatment profiles and/or patient-specific treatment plans, such as those described, for example, in commonly assigned U.S. Pat. No. 8,275,442. In some embodiments, the controller 114 can be incorporated into the applicator 102 of another component of the apparatus 100.

C. Stress Relief Couplings

FIG. 3 is an isometric view of the coupling 107 in accordance with some embodiments the technology. The coupling 107 can include swivel connectors 117a, 117b (collectively "swivel connectors 117"), a clamp 141, and retainers 143a, 143b (collectively "retainers 143"). The retainer 143a couples the conduit end 121 to the swivel connector 117a, and the retainer 143b couples the conduit end 123 to the swivel connector 117b. The conduit ends 121, 123 are rotatable relative to one another, as indicated by arrows 171, 173. In some embodiments, the swivel connector 117a is fixed (e.g., rotationally fixed, translationally fixed, etc.) to the conduit end 121 such that the swivel connector 117a and conduit end 121 rotate in unison. The swivel connector 117b can be fixed to the conduit end 123 such that the swivel connector 117b and conduit end 123 rotate in unison.

Figure 4:
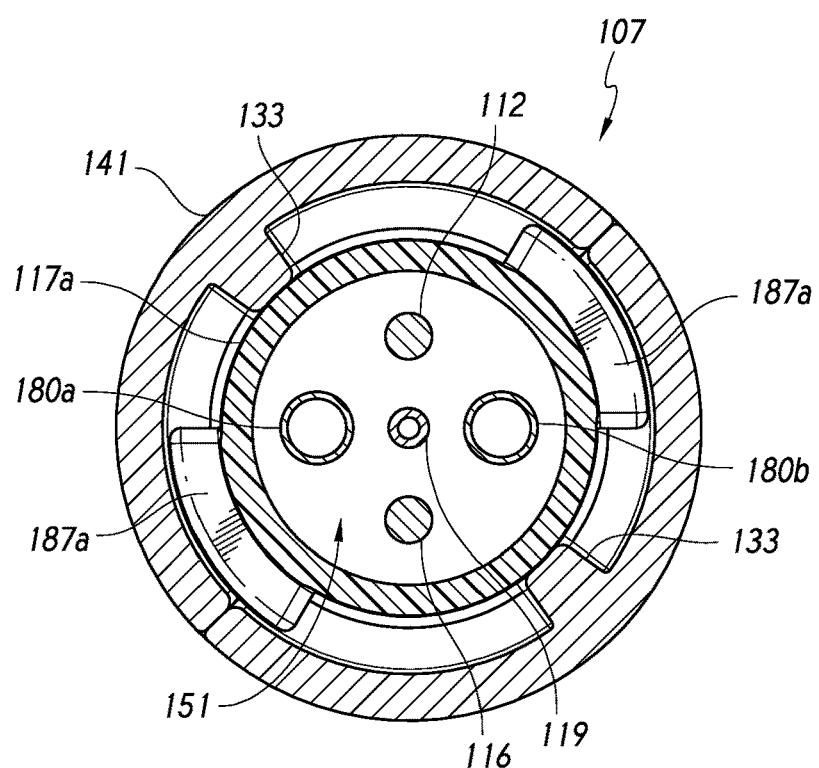
FIG. 4 is a cross-sectional view of the stress relief coupling taken along line 4-4 of FIG. 1.
Figure 5:
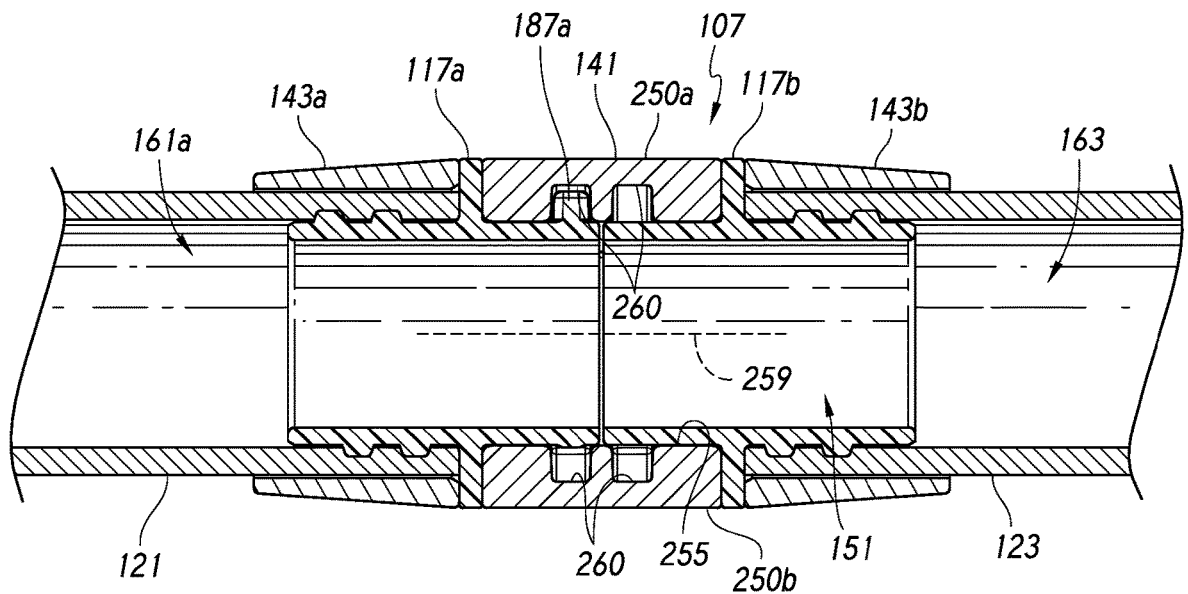
FIG. 5 is a cross-sectional view of the stress relief coupling taken along line 5-5 of FIG. 1.

FIG. 4 is a cross-sectional view of the coupling 107 taken along line 4-4 of FIG. 1 in accordance with at least some embodiments of the technology. FIG. 5 is a cross-sectional view of the coupling 107 taken along line 5-5 of FIG. 1 with internal elements of the conduit 104 shown removed. Referring to FIG. 4, the electrical line 112, control line 116, vacuum tube 119, and fluid lines 180a, 180b are located in a lumen 151 of the coupling 107. Other internal elements can also pass through the lumen 151.

The clamp 141 and the swivel connectors 117 together have tabs (tab 187a of swivel connector 117a is identified in FIGS. 4 and 5) and stops (stops 133 of the clamp 141 is identified in FIG. 4) that allow the conduit ends 121, 123 to rotate relative to each other through an angle so as to minimize or limit a rotational force exerted on the applicator. The angle can be in a range from about 20 degrees to about 340 degrees. In some embodiments, the angle is between about 45 degrees to about 315 degrees, about 90 degrees to about 270 degrees, about 135 degrees to about 225 degrees, or about 160 degrees to about 200 degrees. In certain embodiments, the conduit ends 121, 123 rotate relative to each other through an angle that is greater than either 0, 45, 90, 135, or 179 degrees, and less than either 360, 315, 270, 225, or 181 degrees. The configuration and location of the tabs and stops can be selected to achieve the desired angular rotation of the swivel connectors 117a, 117b about internal elements extending through the conduit lumen 161 (FIG. 5), a coupling lumen 151 (FIGS. 4 and 5), and a conduit lumen 163 (FIG. 5).

Figure 6:
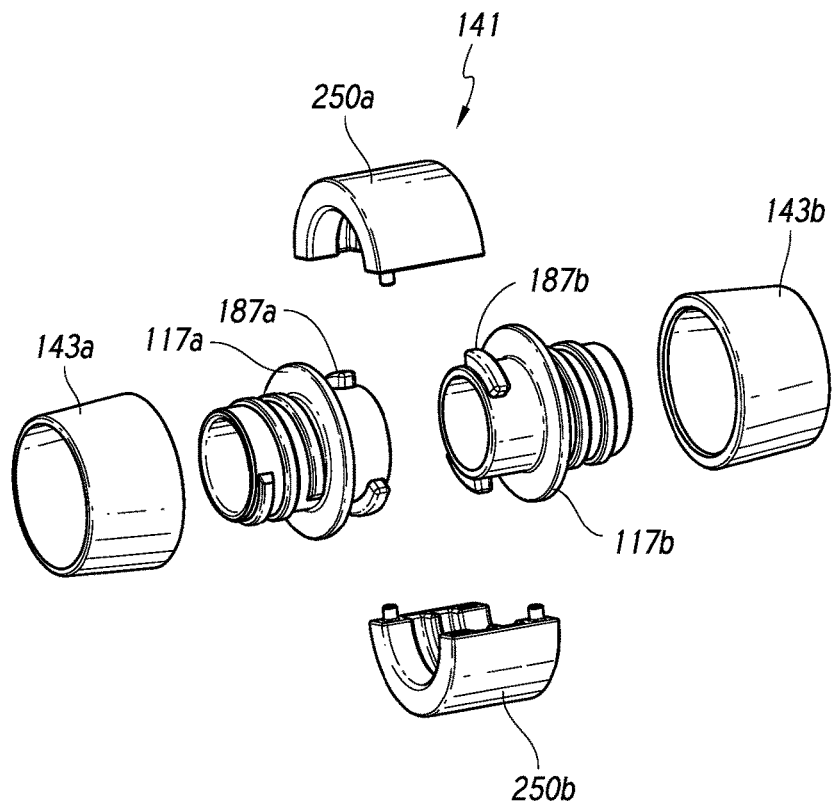
FIG. 6 is an exploded isometric view of a stress relief coupling in accordance with some embodiments of the technology.
Figure 7:
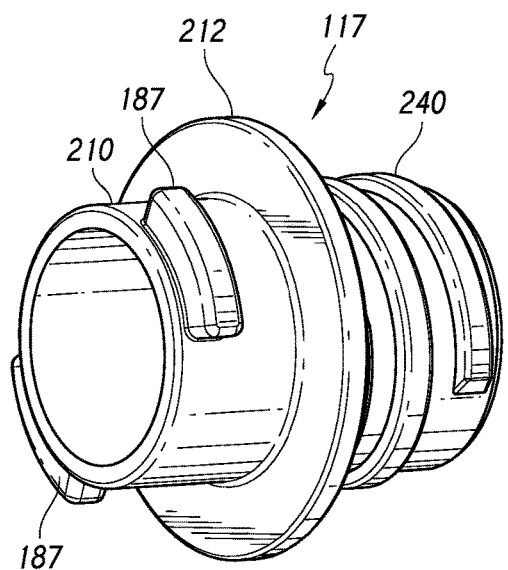
FIG. 7 is an isometric view of a swivel connector in accordance with some embodiments of the technology.
Figure 8:
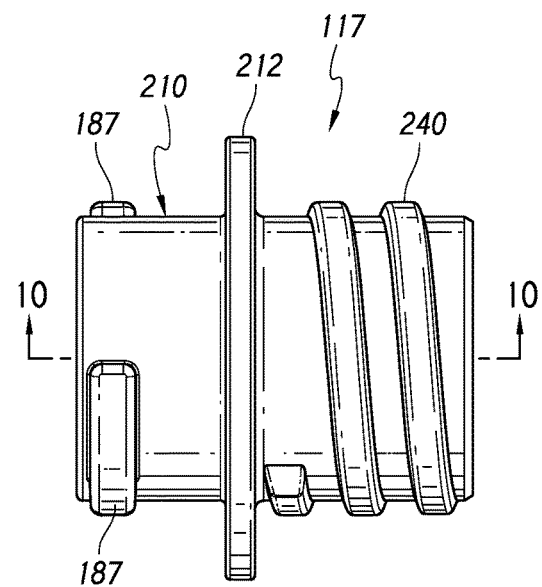
FIG. 8 is a top view of the swivel connector of FIG. 7.
Figure 9:
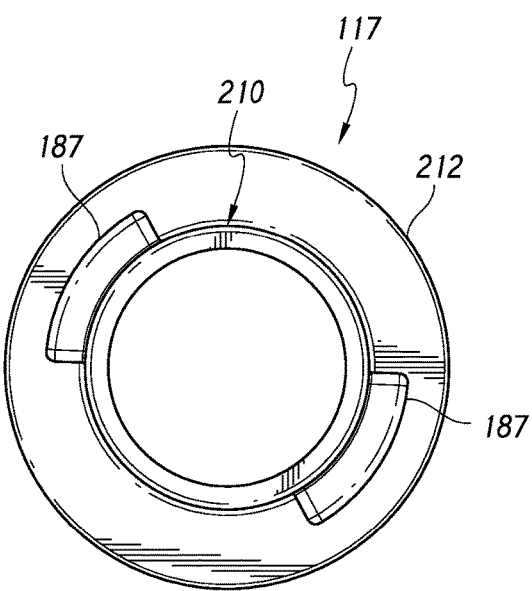
FIG. 9 is a front view of the swivel connector of FIG. 7.
Figure 10:
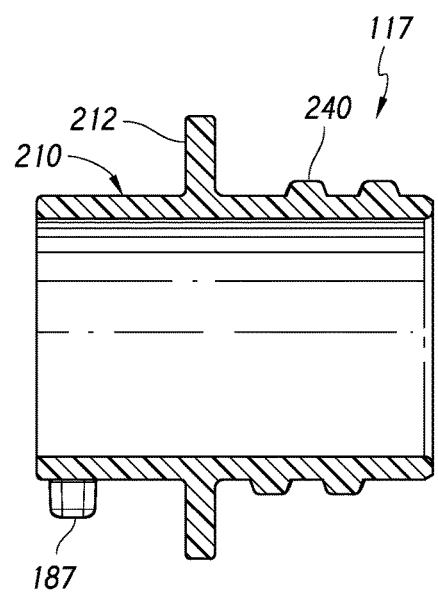
FIG. 10 is a cross-sectional view of the swivel connector taken along line 10-10 of FIG. 8.

FIG. 6 is an exploded isometric view of the coupling 107. Referring to FIGS. 5 and 6 together, the clamp 141 includes semi-cylindrical shells 250a, 250b configured to be located between the retainers 143a, 143b and surround ends of the swivel connectors 117. Referring now to FIG. 5, the shells 250a, 250b can be connected to form a cylinder with an interior bore 255 and circular channels 260 which extend around an axis 259 of the bore 255.

FIGS. 7-10 show a swivel connector 117 in accordance with some embodiments of the technology. The swivel connector 117 can include a cylindrical outer surface 210 and radially protruding tabs 187, which extend outwardly from the cylindrical outer surface 210. A flange 212 can be positioned between the two tabs 187 and external threads 240. The swivel connector 117 can include two tabs 187 (illustrated), one tab, or more than two tabs.

Figure 11:
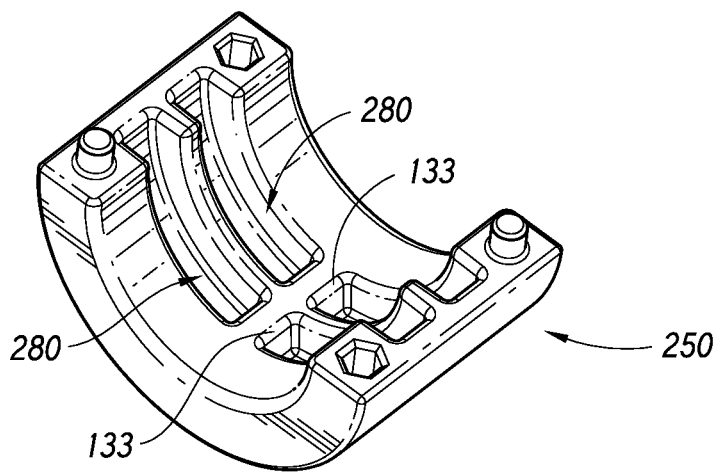
FIG. 11 is an isometric view of a clamp shell in accordance with some embodiments of the technology.
Figure 12:
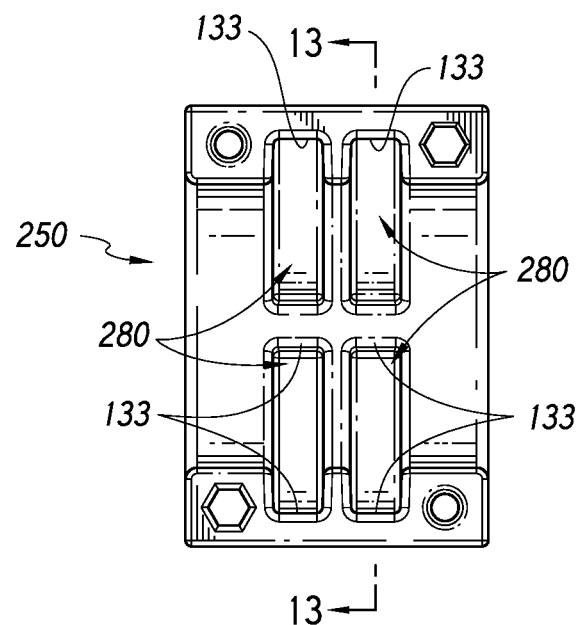
FIG. 12 is a top view of the clamp shell of FIG. 11.
Figure 13:
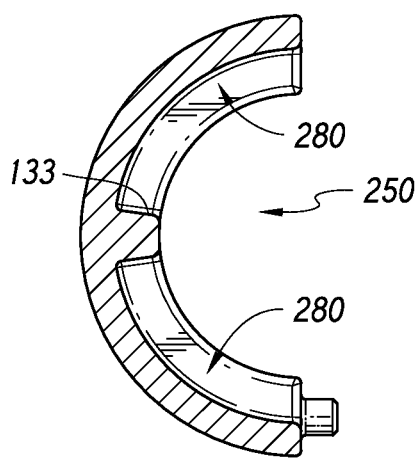
FIG. 13 is a cross-sectional view of the clamp shell taken along line 13-13 of FIG. 12.

FIGS. 11-13 show a clamp shell 250 in accordance with some embodiments the technology. The clamp shell 250 can include arcuate channels 280 with stops 133 formed therein, such that when the swivel connectors 117 and the clamp 141 are assembled, tabs (e.g., tabs 187 of FIG. 7-10) are seated in and can slide along the channels 280 to allow the swivel connectors 117 to rotate relative to shells 250.

D. Methods of Treating Tissue

Referring again to FIG. 1, the applicator 102 can be positioned at a treatment site and can draw in tissue using vacuum provided by the pressurization device 113 until the tissue is in thermal contact with temperature controlled surfaces/elements of the applicator 102. If the applicator 102 is located under the patient's chin 96, the connector 103 can lay across the patient's chest or torso. The patient's body can be periodically repositioned to avoid discomfort during relatively long treatment periods (e.g., treatment periods longer than 30 minutes). The coupling 107 can swivel to keep twisting of conduit sections 109, 111 at or below acceptable levels.

The applicator 102 can extract heat from tissue so as to cool target tissue an amount sufficient to be biologically effective in damaging and/or reducing subcutaneous lipid-rich cells. The applicator 102 can also be used at a wide range of treatment sites, including sites located along the neck, hips, thighs, stomach, etc. Exemplary treatment sites, applicators, methods of treatment, and components and features that can be incorporated into the system systems disclosed herein are described in, e.g., commonly assigned U.S. Pat. No. 7,854,754 and U.S. Patent Publication Nos. 2008/0077201, 2008/0077211, 2008/0287839, 2011/0238050 and 2011/0238051. Applicators disclosed herein can include elements (e.g., electrodes, vibrators, etc.) for delivering energy, such as radiofrequency energy, ultrasound energy (e.g., low frequency ultrasound, high frequency ultrasound, etc.), mechanical massage, and/or electric fields. The energy can be selected to affect treatment by, for example, heating tissue. Additionally or alternatively, energy can be used to affect the crystal formation in non-targeted tissues while allowing cooling of the targeted tissue. In non-targeted cells or structures, non-thermal energy parameters may be selected to reduce ice crystal size and/or length, reduce freezing lethality, or the like. In targeted cells or structures, non-thermal energy parameters may be selected to enhance crystal nucleation. Thus, energy can be selectively applied to control therapy.

Without being bound by theory, the selective effect of cooling disclosed herein is believed to result in, for example, membrane disruption, cell shrinkage, disabling, damaging, destroying, removing, killing and/or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling can be the selectively reduction of lipid-rich cells by a desired mechanism of action, such as apoptosis, lipolysis, or the like. In some procedures, the applicator 102 can cool the tissue of the subject 101 to a temperature in a range of from about −25° C. to about 20° C. In other embodiments, the cooling temperatures can be from about −20° C. to about 10° C., from about −18° C. to about 5° C., from about −15° C. to about 5° C., or from about −15° C. to about 0° C. In further embodiments, the cooling temperatures can be equal to or less than −5° C., −10° C., −15° C., or in yet another embodiment, from about −15° C. to about −25° C. Other cooling temperatures and temperature ranges can be used.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or dysfunction, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" Heart Failure Reviews, 8, 277-284 (2003). Other possible mechanisms of adipocyte damage, described in U.S. Pat. No. 8,192,474, relate to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation as a result of applied pressure, cooling which may affect vasoconstriction in the cooled tissue, or the like. In addition to the ischemic damage caused by oxygen starvation and the buildup of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic, or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" Aviation, Space and Environmental Medicine 70, 42-50 (1999).

One expected advantage of the foregoing techniques is that the subcutaneous lipid-rich cells in the target region can be reduced generally without collateral damage to non-lipid-rich cells in the same region. In general, lipid-rich cells can be affected at low temperatures that do not affect non-lipid-rich cells. As a result, lipid-rich cells, such as those associated with highly localized adiposity (e.g., submental adiposity, submandibular adiposity, facial adiposity, etc.), can be affected while non-lipid-rich cells (e.g., myocytes) in the same generally region are not damaged. The unaffected non-lipid-rich cells can be located underneath lipid-rich cells (e.g., cells deeper than a subcutaneous layer of fat), in the dermis, in the epidermis, and/or at other locations.

In some procedures, the apparatus 100 can remove heat from underlying tissue through the upper layers of the skin and create a thermal gradient with the coldest temperatures near the cooling surface, or surfaces, of the applicator 102 (i.e., the temperature of the upper layer(s) of the skin can be lower than that of the targeted underlying target cells). It may be challenging to reduce the temperature of the targeted cells low enough to be destructive to these target cells (e.g., induce apoptosis, cell death, etc.) while also maintaining the temperature of the upper and surface skin cells high enough so as to be protective (e.g., non-destructive). The temperature difference between these two thresholds can be small (e.g., approximately, 5° C. to about 10° C., less than 10° C., less than 15° C., etc.). Protection of the overlying cells (e.g., typically water-rich dermal and epidermal skin cells) from freeze damage during dermatological and related aesthetic procedures that involve sustained exposure to cold temperatures may include improving the freeze tolerance and/or freeze avoidance of these skin cells by using, for example, cryoprotectants for inhibiting or preventing such freeze damage. The apparatus 100 can perform medical treatments for provide therapeutic effects and/or cosmetic procedures for cosmetically beneficial effect.

The couplings disclosed herein can be used with invasive applicators that include one or more cryoprobes, electrodes, injectors (e.g., needles) and/or other invasive components that can be inserted directly into the targeted tissue (e.g., subcutaneous adipose tissue) to cool, freeze, or otherwise thermally process the targeted tissue. Liquids and/or energy can be delivered through the coupling to operate such invasive components. The treatment systems disclosed herein may be used with a substance that may provide a thermal coupling between the subject's skin and the thermal element(s) to improve heat transfer therebetween. The substance may be a fluid, e.g., a liquid, a gel, or a paste, which may be hygroscopic, thermally conductive, and biocompatible.

E. Conclusion

It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the construction of the phrase "at least one of A, B, and C, etc." should be broad (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, the construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

Any patents, applications, and other references, including any that may be listed in accompanying filing papers, are incorporated herein by reference. Aspects of the described technology can be modified, if necessary, to employ the systems, functions, and concepts of the various references described above to provide yet further embodiments. These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

What is claimed is:

1. An apparatus for treating a patient, comprising:
a base unit connectable to electrical power;
an applicator connectable to a patient's skin;
a conduit containing one or more electrical wires and tubing connected to the applicator and the base unit; and
a stress relief coupling connected to the conduit at a location remote from the applicator and the base unit which allows a first section of the conduit located between the applicator and the stress relief coupling to rotate relative to a second section of the conduit located between the stress relief coupling and the base unit so as to reduce rotational forces imparted to the applicator from its connection with the conduit, wherein the stress relief coupling extends along a longitudinal axis and includes first and second swivel connectors rotatably fixed to the first and second sections, respectively,
wherein the first swivel connector includes a first outer surface portion, a second outer surface portion, a first flange separating the first outer surface portion from the second outer surface portion and extending outwardly away from the longitudinal axis, and a first tab extending outwardly from the first outer surface portion away from the longitudinal axis, and
wherein the second swivel connector includes a third outer surface portion, a fourth outer surface portion, a second flange separating the third outer surface portion from the fourth outer surface portion and extending outwardly away from the longitudinal axis, and a second tab extending outwardly from the third outer surface portion away from the longitudinal axis,
first and second retainers coupled to the first and second swivel connectors, respectively,
wherein the first section of the conduit extends at least partially between the second outer surface and the first retainer, and
wherein the second section of the conduit extends at least partially between the fourth outer surface and the second retainer, and
a clamp coupled to the first and second swivel connectors between the first and second flanges so as to connect the first and second sections of the conduit together,
wherein the clamp includes a first channel extending partially around the longitudinal axis and a second channel extending partially around the longitudinal axis,
wherein the first tab is seated within the first channel and the second tab is seated within the second channel to allow the first and second sections of the conduit to rotate relative to each other through an angle only within a range of about 20 degrees to about 340 degrees about the longitudinal axis.

2. The apparatus of claim 1, wherein the applicator and the base unit are each connected to the conduit so as to be rotationally fixed thereto, wherein a length of the conduit between the applicator and the stress relief coupling is greater than 1 foot and less than 5 feet.

3. The apparatus of claim 1, wherein the first and second swivel connectors are rotatable about the one or more electrical lines and tubing which extend through the coupling lumen.

4. The apparatus of claim 1, further comprising:
a first fastener connecting the first section of the conduit to the applicator such that an applicator end of the first section is rotationally fixed relative to the applicator; and
a second fastener connecting the second section of the conduit to the base unit such that a base unit end of the second section is rotationally fixed relative to the base unit.

5. The apparatus of claim 1, wherein the stress relief coupling is attached to the conduit at a point displaced from and remote from the applicator so that as first and second ends of the conduit are rotated relative to one another significant rotational forces are not exerted on connections between the one or more electrical wires and tubing housed in the conduit and the applicator, and wherein the tubing includes a vacuum tube and a tube for transmitting a liquid.

6. The apparatus of claim 1, wherein
the clamp includes first and second semi-cylindrical shells configured to form a cylinder with an interior bore.

7. The apparatus of claim 1, wherein the conduit includes first and second conduit ends that rotate relative to each other through an angle greater than either 45, 90, 135, or 179 degrees, and less than either 315, 270, 225, or 181 degrees.

8. The apparatus of claim 1, wherein a length of the first section is greater than 1 foot and less than 5 feet.

9. The apparatus of claim 1 wherein the first tab is configured to slide along an entire length of the first channel, and wherein the second tab is configured to slide along an entire length of the second channel.

10. The apparatus of claim 9 wherein a first angle about the longitudinal axis between a first end of the first channel and a second end of the first channel is within the range of about 20 degrees to about 340 degrees, and wherein a second angle about the longitudinal axis between a first end of the second channel and a second end of the second channel is within the range of about 20 degrees to about 340 degrees.

11. The apparatus of claim 1 wherein the clamp abuts a first side portion of the first flange and a first side portion of the second flange, wherein the first retainer abuts a second side portion of the first flange, and wherein the second retainer abuts a second side portion of the second flange.

12. The apparatus of claim 1 wherein the first and second channels extend to a first distance from the longitudinal axis, and wherein the first and second flanges extend to a second distance from the longitudinal axis greater than the first distance.

13. The apparatus of claim 1 wherein the clamp, the first retainer, and the second retainer together define a generally contiguous outer surface of the stress relief coupling.

14. An apparatus for treating a patient, comprising:
a base unit;
an applicator connectable to a patient's skin;
a conduit containing one or more electrical wires and tubing connected to the applicator and the base unit; and
a stress relief coupling connected to a first section and a second section of the conduit,
wherein the stress relief coupling has a longitudinal axis and includes
a first swivel connector rotatably fixed to the first section, wherein the first swivel connector includes a first outer surface portion, a second outer surface portion, a first flange separating the first outer surface portion from the second outer surface portion and extending outwardly away from the longitudinal axis, and a first tab extending outwardly from the first outer surface portion away from the longitudinal axis,
a second swivel connector rotatably fixed to the second section, wherein the second swivel connector includes a third outer surface portion, a fourth outer surface portion, a second flange separating the third outer surface portion from the fourth outer surface portion and extending outwardly away from the longitudinal axis, and a second tab extending outwardly from the third outer surface away from the longitudinal axis, and
a clamp positioned between the first and second flanges and including a first channel extending partially around the longitudinal axis and configured to receive the first tab therein and a second channel extending partially around the longitudinal axis and configured to receive the second tab therein, wherein the clamp rotatably connects the first and second swivel connectors together such that the clamp and the first and second swivel connectors cooperate to limit rotation of the first and second sections of the conduit relative to one another to an angle less than about 340 degrees about the longitudinal axis.

15. The apparatus of claim 14, wherein the clamp is configured such that the angle is limited to be only 20 degrees to 340 degrees.

16. The apparatus of claim 14, wherein the clamp substantially prevents axial translation between the first and second swivel connectors while allowing the first and second swivel connectors to rotate relative to one another.

17. The apparatus of claim 14, wherein at least one of the first swivel connector or the second swivel connector is translationally fixed to the clamp.

18. The apparatus of claim 14, wherein the one or more electrical lines and the tubing each extend through the stress relief coupling, and wherein the first and second swivel connectors are rotatable about the one or more electrical lines and the tubing.

19. An apparatus for treating a patient, comprising:
a base unit;
an applicator configured to hold the patient's skin via a vacuum;
a conduit containing one or more electrical wires and a vacuum tube each connected to the applicator and the base unit; and
a stress relief coupling having a longitudinal axis and including
a first swivel connector rotatably fixed to a first section of the conduit, wherein the first swivel connector includes a first outer surface portion, a second outer surface portion, a first flange separating the first outer surface portion from the second outer surface portion and extending outwardly away from the longitudinal axis, and a first projection projecting outwardly from the first outer surface portion away from the longitudinal axis,
a second swivel connector rotatably fixed to a second section of the conduit, wherein the second swivel connector includes a third outer surface portion, surface portion from the fourth outer surface portion and extending outwardly away from the longitudinal axis, and a second projection projecting outwardly from the third outer surface portion away from the longitudinal axis, and
a clamp positioned between the first and second flanges and including a first channel extending only partially around the longitudinal axis and a second channel extending only partially around the longitudinal axis, wherein the first channel receives the first tab and the second channel receives the second tab to (a) rotatably connect the first and second swivel connectors together and (b) limit rotation between the first and second swivel connectors to an angle less than about 360 degrees.

20. The apparatus of claim 19, wherein the clamp allows rotation between the first and second swivel connectors while the vacuum tube remains open to maintain the vacuum between the applicator and the patient's skin.

* * * * *